United States Patent [19]

Rubino

[11] 3,998,788
[45] Dec. 21, 1976

[54] ALUMINUM-ZIRCONIUM ANTI-PERSPIRANT SYSTEMS WITH TRACE AMOUNTS OF ALKALINE EARTH METALS

[75] Inventor: Andrew M. Rubino, New Providence, N.J.

[73] Assignee: Armour Pharmaceutical Company, Phoenix, Ariz.

[22] Filed: July 17, 1974

[21] Appl. No.: 489,320

Related U.S. Application Data

[63] Continuation-in-part of Ser. No. 411,995, Nov. 1, 1973, Ser. No. 418,712, Nov. 23, 1973, Ser. No 431,639, Jan. 8, 1974, Ser. No. 433,931, Jan. 16, 1974, and Ser. No. 477,544, June 7, 1974.

[52] U.S. Cl. .............................. 424/47; 260/429.3; 423/351; 424/66; 424/68
[51] Int. Cl.$^2$ ........................................ A61K 7/32
[58] Field of Search .................... 424/47; 423/351; 260/429.3

[56] References Cited

UNITED STATES PATENTS

| | | | |
|---|---|---|---|
| 38,748 | 6/1863 | Kidwell | 424/76 X |
| 2,294,140 | 12/1940 | Taylor | 424/65 X |
| 2,314,125 | 3/1943 | Coca | 424/65 |
| 2,350,047 | 5/1944 | Klarmann et al. | 424/65 |
| 2,880,136 | 3/1959 | Gore | 424/156 |
| 3,555,146 | 1/1971 | Jones et al. | 424/67 X |

FOREIGN PATENTS OR APPLICATIONS 2,035,901  12/1970  France ................................ 424/47

*Primary Examiner*—Dale R. Ore
*Attorney, Agent, or Firm*—Frank T. Barber; William W. Schwarze

[57] ABSTRACT

Unusually effective anti-perspirant compositions are provided by forming an astringent complex of a basic aluminum compound, a zirconium compound and a trace amount of an alkaline earth metal salt. The alkaline earth metal may be either calcium or magnesium or both, but preferably magnesium, and may be added as any of the usual salts such as halides, carbonate, oxide, hydroxide, etc. The basic aluminum compounds may be any of the usual basic aluminum anti-perspirant salts, particularly basic aluminum halides, and the zirconium compound may be a zirconium oxy salt and/or zirconium hydroxy salt. The complex should have an Al/Zr mole ratio of about 10:1 to 1:10, and preferably about 4:1 to 1:1, and the pH of an aqueous solution containing 5 to 15 weight percent of the complex (based on the oxides of aluminum and zirconium) should be at least about 3. The complexes may be used in conventional anti-perspirant forms, including aqueous solutions, aerosol sprays (including powder-in-oil aerosol sprays), as well as creams, lotions and cream sticks.

18 Claims, No Drawings

ALUMINUM-ZIRCONIUM ANTI-PERSPIRANT SYSTEMS WITH TRACE AMOUNTS OF ALKALINE EARTH METALS

CROSS-REFERENCE TO RELATED APPLICATIONS

This application is a continuation-in-part of my following copending applications: Ser. No. 411,995, filed Nov. 1, 1973, entitled "Basic Magnesium-Aluminum Compositions Useful As Anti-Perspirants"; Ser. No. 418,712, filed Nov. 23, 1973, entitled "Aluminum-Zirconium Anti-Perspirant Systems With Salts Of Amino Acids"; Ser. No. 431,639, filed Jan. 8, 1974, entitled "Zirconium-Aluminum-Polyol Buffered Anti-Perspirant Complexes"; Ser. No. 433,931, filed Jan. 16, 1974, entitled "Aluminum-Zirconium Anti-Perspirant Systems With Hydroxy Carboxylic Compounds"; and Ser. No. 477,544, filed June 7, 1974, entitled "Aluminum-Zirconium Anti-Perspirant Systems With Complex Aluminum Buffers".

BACKGROUND OF THE INVENTION

The present invention relates to aluminum zirconium anti-perspirant systems with trace amounts of alkaline earth metals. More particularly, the invention is directed to unusually effective aluminum-zirconium anti-perspirant complexes fortified with salts of alkaline earth metals such as magnesium and calcium.

It has been known in the art for some time that zirconium salts provide exceptionally effective anti-perspirant properties. Such zirconium salts have included particularly the acidic zirconium salts, such as zirconium oxy chloride or zirconyl chloride, zirconium hydroxy chloride, and other halide and sulfate substitutes of these salts.

To date, the most effective and acceptable anti-perspirant systems containing zirconium have been those in which the zirconium salts have been combined in various forms with basic aluminum compounds, either in solutions or complexes of the salts. Examples of such aluminum-zirconium anti-perspirant systems are described in U.S. Pat. Nos. 2,814,584 and 2,814,585 to Daley, 2,854,382 to Grad, 2,906,668 to Beekman, 3,405,153 to Jones and Rubino, and 3,792,068 to Luedders et al. More recently, I have described a number of new buffered aluminum-zirconium anti-perspirant complexes in my copending applications Ser. Nos. 418,712; 431,639; 433,931 and 477,544.

Despite the effectiveness of zirconium compounds in anti-perspirant systems, the most effective anti-perspirant systems found to date (which are not too acidic to apply to the skin) have only had an effectiveness in the range of about 30 to 45 percent perspiration inhibition. Accordingly, the anti-perspirant art has continuously attempted to obtain even more effective anti-perspirant compositions.

BRIEF SUMMARY OF THE INVENTION

It has now unexpectedly been found that exceptionally effective anti-perspirant compositions can be formed by fortifying aluminum-zirconium anti-perspirant complexes with trace amounts of salts of an alkaline earth metal. Such complexes are formed from a basic aluminum compound, a zirconium compound selected from zirconium oxy salts, zirconium hydroxy salts and mixtures thereof, and trace amounts of a salt of an alkaline earth metal selected from magnesium, calcium and mixtures thereof. The aluminum and zirconium compounds are present in such amounts as to yield an Al/Zr mole ratio of about 10:1 to 1:10, and preferably about 4:1 to 1:1.

The alkaline earth metal, preferably magnesium, need not be present in an amount any greater than about 1 part by weight to 30 parts by weight of aluminum plus zirconium. Stated otherwise, a 10 weight percent solids solution of the anti-perspirant complex need contain no more than about 0.1 weight percent of the alkaline earth metal.

The presence of magnesium and/or calcium salts in anti-perspirant systems is not entirely new. For example, U.S. Pat. No. 2,350,047 to Klarmann et al. suggests the use of magnesium oxide, hydroxide or carbonate in small amounts (from about 1 to 3 percent) in anti-perspirant solutions or creams containing certain astringent aluminum salts. The magnesium compounds in this patent were alleged to reduce the deteriorating effects of the aluminum compounds on fabrics. Similarly, U.S. Pat. No. 2,571,030 to Govett et al. suggested the formation of double complexes between aluminum chloride and calcium or magnesium chloride to reduce the corrosive effects on fabrics of anti-perspirant cream compositions containing the aluminum chloride. This patent suggests the use of about 0.2 to 15 parts by weight of magnesium or calcium halide to 100 parts of aluminum.

More recently, my copending application Ser. No. 411,995 describes basic aluminum anti-perspirant compositions in which magnesium salts have been substituted for a portion of the aluminum salts to synergistically achieve aluminum-magnesium anti-perspirant systems of comparable effectiveness. In such application the magnesium salts are present in amounts such that the $Al_2O_3/MgO$ ratio is in the range of about 4:1 to 1:4. In addition, several of my other abovementioned copending patent applications, including particularly Ser. No. 477,544, describe the use of various magnesium and calcium compounds and complexes as buffers in aluminum-zirconium anti-perspirant systems.

However, to my knowledge, no one has previously found or recognized that trace amounts of alkaline earth metal salts, such as magnesium and calcium, could dramatically improve the anti-perspirant effectiveness of aluminum-zirconium anti-perspirant systems. This synergistic effect of the alkaline earth metals on aluminum-zirconium complexes was completely unexpected to me.

DETAILED DESCRIPTION OF PREFERRED EMBODIMENTS

The basic aluminum compounds which may be used in forming the complexes of the present invention include the conventional basic aluminum salts which have been known to the anti-perspirant art for some time, and which have a degree of anti-perspirant efficacy in their own right, as a result of the presence of the active aluminum ion. These basic aluminum salts may be represented by the following general empirical formula:

$$Al_2(OH)_{6-nx} A_x$$

wherein $x$ may vary from greater than 0 to less than 6, $6-nx$ is greater than or equal to 0, $n$ is the valence of A, and A is selected from the group consisting of halides, nitrate, sulfamate, sulfate and mixtures thereof.

It will of course be understood that the above formula is greatly simplified and is intended to represent and include basic aluminum compounds containing coordinated and/or bound molecules of water as well as polymers, complexes and mixtures of the above basic formula.

Particularly preferred basic aluminum compounds of the above formula are the 2/3 to 5/6 basic aluminum chlorides, in which A is chloride and $x$ is between about 1 and 2 and need not be an integer. Thus, such basic aluminum chlorides may be represented by the formulas

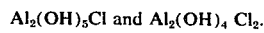

$$Al_2(OH)_5Cl \text{ and } Al_2(OH)_4Cl_2.$$

The basic aluminum chlorides are also referred to as aluminum chlorhydroxide or aluminum chlorhydrate or aluminum hydroxy chloride, and are commercially available from Reheis Chemical Company, Division of Armour Pharmaceutical Company under the trademark "Chlorhydrol".

In addition to the simple basic aluminum salts indicated above, complexes or derivatives of the basic aluminum salts may also be used advantageously in the complexes of the present invention. Examples of such derivatives or complexes include the phenolsulfonate derivatives described in U.S. Pat. No. 3,634,480 to Sheffield. Such complexes are formed by reacting 5/6 basic aluminum chloride with phenolsulfonic acid, zinc phenolsulfonate or aluminum phenolsulfonate. Other suitable derivatives and complexes of basic aluminum salts which may be used in the complexes of the present invention will be readily apparent to those of ordinary skill in the art in view of the present invention.

The zirconium compounds which are useful in forming the complexes of the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein $z$ may vary from about 0.9 to 2 and need not be an integer, $n$ is the valence of B, $2-nz$ is greater than or equal to 0, and B may be the same as A in the previous formula. That is, B may be selected from the group consisting of halides, nitrate, sulfamate, sulfate and mixtures thereof. Although only zirconium compounds are exemplified in this specification, it will be understood that other Group IV B metals, including hafnium could be used to form the complexes of the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxyl group, varying from about 1.1 to only slightly greater than 0 groups per zirconium atom.

Particularly preferred zirconium compounds for use in the present invention include zirconyl chloride (also referred to as basic zirconium chloride or zirconium oxy chloride) and zirconyl hydroxy chloride, which may be represented by the simple formulas $ZrOCl_2$ and $ZrO(OH)Cl$, respectively. These compounds are commercially available in solution form. In the alternative, the zirconium compounds can be made by dissolution of commercially available zirconium carbonate paste (carbonated hydrous zirconia) in the appropriate amount of the acid of the anion to be used, e.g., hydrochloric acid. Other useful zirconium salts will be apparent to those of ordinary skill in the art, such as trioxodizirconium hydroxy halides and similar salts described, for example, in U.S. Pat. No. 2,837,400 to Blumenthal.

The salt of an alkaline earth metal may be a salt of either magnesium or calcium, but preferably magnesium. The anion of the metal salt is not particularly crucial and may be any of the halides, such as chloride or bromide, nitrate, carbonate, hydroxide, oxide, sulfamate, phenolsulfonate, or others. The anion should not however occlude the alkaline earth metal in solution, but rather the salt should be such as to produce a highly ionized alkaline earth metal in an acidic solution.

The alkaline earth metal need only be present in the complexes of the present invention in trace amounts. The exact limits of the trace amounts are not presently known. However, as used herein, trace amounts will be understood to include anywhere from about 1 part by weight of alkaline earth metal to 1,000 parts by weight of aluminum plus zirconium to about 1 part by weight of alkaline earth metal to about 30 parts by weight of aluminum plus zirconium. Stated otherwise, a solution containing the complexes to the extent of about 5 to 15 weight percent aluminum plus zirconium (calculated as the oxides, $Al_2O_3$ and $ZrO_2$) will contain only about 0.001 to 0.1 weight percent magnesium or other alkaline earth metal.

The relative amounts of basic aluminum compound and zirconium compound to be added to form the complexes of the present invention should be such as to yield an Al/Zr mole ratio of between about 10:1 and 1:10, and preferably about 4:1 to 1:1. Although higher ratios of zirconium would be desirable in the complex from the standpoint of anti-perspirant efficacy, it will be appreciated that zirconium is considerably more expensive than aluminum. In addition, where higher ratios of zirconium are present in the complex, the acidity of the anti-perspirant composition becomes a problem and it will be necessary to add buffers in order to obtain a satisfactory pH. That is, it is generally accepted that to be satisfactory for application to the human skin, an anti-perspirant composition must have a pH of at least about 3 and preferably between about 3 and 5.

Although the alkaline earth metal salts are generally satisfactory as buffers for aluminum-zirconium anti-perspirant systems, the trace amounts present in the complexes of the present invention are insufficient to appreciably affect the pH of the anti-perspirant composition. In the event that a buffer is necessary, a number of buffers for aluminum-zirconium anti-perspirant systems are available in the art. For example, the compositions may be buffered with urea or water soluble amino acids, according to U.S. Pat. Nos. 2,814,584; 2,814,585 and 2,854,382. More effective and sophisticated buffers for aluminum-zirconium systems are also described in my copending applications Ser. Nos. 418,712; 431,639; 433,931 and 477,544. In addition, if desired the pH of the anti-perspirant composition may be raised or lowered by adding additional aluminum compounds to the reaction mixture in the formation of the complexes of the present invention. For example, aluminum chloride ($AlCl_3$) may be added to lower the pH or aluminum hydroxide ($Al(OH)_3$) may be used to raise the pH.

The method of forming the complexes of the present invention is not particularly critical. In general, the complexes may be formed simply by adding the various components together in an aqueous solution and then, if desired, drying the solution to a dry powder. The various components are preferably added one at a time with stirring or agitation. Moderate heating, such as to a maximum of about 75° or 85° C. for up to a half hour may be advantageous after addition of certain ingredients, particularly when an insoluble compound is added or when a precipitate is formed after the addition of an ingredient.

The drying step is not particularly critical and may be carried out in a number of different ways, including vacuum drying, oven drying, spray drying or freeze drying. It will be understood that drying does not mean that all of the water is removed, since a certain amount of water should remain in the complex as coordinated and/or bound water. Thus, drying to just past the point where the solution becomes a friable solid should be sufficient. If the complex is over dried, so that some of the coordinated and/or bound water is removed, the stability and/or activity of the complex may be interferred with, and the complex may not be readily redissolvable in solvents, particularly hydro-alcoholic solvents.

While it has been indicated that the reaction process is not considered particularly critical, it will be understood that sufficient time, heat and agitation are needed to allow reaction of the salts to form the new complexes of the present invention.

The complexes of the present invention will now be illustrated in more detail with references to the following specific, non-limiting example:

100 grams of a 0.5 weight percent slurry of basic magnesium carbonate were prepared. To this slurry was added with agitation 200 grams of a 25 weight percent solution of aluminum chlorhydrate (5/6 basic aluminum chloride). The resulting solution was stirred until clear, and then heated to 80° centigrade prior to the addition of 73 grams of a zirconyl chloride solution (14.4 weight percent zirconium). After cooling, this product solution was oven dried at 55° centigrade under a vacuum of 45 cm of Hg. The dried material assayed 15.3 percent Al, 13.5 percent Zr and 0.08 percent Mg. An aqueous solution containing 10 weight percent of this dried complex had a pH of 4.0.

The anti-perspirant effectiveness of the above astringent composition was tested by an independent testing laboratory by axillary application to a number of women from the Miamiville, Ohio area. The test procedure used to determine the anti-perspirant effectiveness is a standard one now known to the art, and described in more detail in my copending applications Ser. Nos. 411,995 and 88,206, filed Nov. 9, 1970 in the name of John L. Jones and Andrew M. Rubino for "Basic Aluminum Bromide Compositions". The tests were done simultaneously for comparison on four different anti-perspirant compositions as follows:

Sample A — A 10 percent w/w aqueous solution of a complex of aluminum chlorhydrate (5/6 basic aluminum chloride) and zirconium hydroxy chloride.

Sample B — a 10 percent w/w aqueous solution of a complex of aluminum chlorhydrate (5/6 basic aluminum chloride) and zirconyl chloride.

Sample C — A 10 percent w/w aqueous solution of the complex formed by the specific example above, namely a complex of aluminum chlorhydrate (5/6 basic aluminum chloride), zirconyl chloride and a trace amount of magnesium carbonate.

Sample D — A 10 percent w/w aqueous solution of 5/6 basic aluminum chloride.

All samples were applied at the rate of 0.5 milliliters per application. The test procedure is such as to provide as far as possible equal conditions for all samples tested. The results of the tests are indicated in Table I below.

TABLE I

| Sample | Wt. % Metals | Al/Zr Mole Ratio | % Sweat Reduction | Confidence Limits (%) |
|---|---|---|---|---|
| A | Al = 1.20<br>Zr = 2.14 | 2.0 | 47.8 | ± 7.8 |
| B | Al = 1.63<br>Zr = 1.39 | 4.0 | 46.6 | ± 9.2 |
| C | Al = 1.53<br>Zr = 1.35<br>Mg = 0.008 | 4.0 | 59.1 | ± 8.2 |
| D | Al = 2.5 | — | 31.6 | ± 15.4 |

The anti-perspirant effectiveness is given in Table I as the percentage sweat reduction or perspiration inhibition. The confidence limits of this effectiveness are given in the last column of Table I. As seen from the weight percent of metals and the Al/Zr mole ratios, samples B and C are substantially identical except for the presence of a trace amount of magnesium in sample C, which represents the anti-perspirant complexes of the present invention. Nevertheless, sample C showed a greatly improved increase in the anti-perspirant efficacy, which is believed to be attributable to the presence of the trace amount of alkaline earth metal.

Although applicant does not wish to be bound by any particular theory, it is believed that the highly ionized alkaline earth metal assists the zirconium to form larger and more highly charged complexes with the aluminum compounds. That is, anti-perspirant theory for some time has associated anti-perspirant efficacy with highly positively charged complexes or polymers of the active ingredient. At very acid or low pH's (e.g., 1–4), zirconium is masked by oxide and hydroxyl groups from the water of the aqueous solution. This masking effect is believed to cause steric problems which prevent efficient complexing of the zirconium with aluminum.

However, at the low pH's mentioned above, polyvalent alkaline metals such as calcium and magnesium are highly ionized and may readily combine with the aluminum. It is believed that these metals in turn provide a link with the zirconium to produce large highly charged anti-perspirant complexes.

As indicated previously, the complexes of the present invention may be used in a variety of conventional anti-perspirant forms which are applied to the human axilla for effective perspiration inhibition. In such formulations, the complex should be present in such amounts that the total aluminum plus zirconium content of the formulation is between about 1.5 and 15 weight percent (depending on the type of formulation employed), calculated as the oxides of the aluminum and zirconium.

For example, aqueous solutions of the complexes may be used in lotions, oil/water creams, and co-dispensing aerosols. The complexes of the present invention are not as a rule soluble in pure alcoholic solvent systems. However, the complexes may be considered for use in hydro-alcoholic solvents. The complexes of the present invention should be present in the above anti-perspirant forms in amounts such that the total content of aluminum plus zirconium in the formulation is on the order of about 5 to 15 weight percent (calculated as the oxides of aluminum and zirconium) or 10 to 30 weight percent of the active ingredient (calculated on a solids basis).

The complexes of the present invention may also be used in the now popular powder-in-oil aerosol sprays. The powder-in-oil systems comprise the dispersion of a finely divided anti-perspirant powder, such as the dried complexes of the present invention, in a non-solubilizing polar organic liquid such as an ester which serves as both a dispersion medium as well as an emollient. The organic liquid coats or wets the powder particles to render them heavier and more occlusive and/or substantive to the axillary region. This primary powder-in-oil suspension, known as the "concentrate", may also include a suspending or anti-compaction agent such as Cab-O-Sil or Bentone 34, to inhibit the dispersed phase from settling and compacting irreversibly. The so-called "extra-dry" formulations use less emollient and higher levels of dry powder, such as talc. Finally, after dynamic agitation the viscous concentrate is generally mixed with about 9 times its weight of a blend of standard propellants.

When used in the powder-in-oil aerosol sprays, the complexes of the present invention should be present in the finished formulation to the extent of about 1 to 6 weight percent, and preferably about 1.5 to 3 weight percent, total aluminum plus zirconium, calculated as the oxides. A typical powder-in-oil aerosol suspension would employ about 5 percent w/w of the active ingredient (dried complex) or about 2.5 percent total oxides.

The present invention may be embodied in other specific forms without departing from the spirit or essential attributes thereof and, accordingly, reference should be made to the appended claims, rather than to the foregoing specification as indicating the scope of the invention.

I claim:

1. A water soluble, astringent complex formed by reacting the following components (a), (b) and (c) in aqueous medium:

a. a basic aluminum compound selected from the group having the general empirical formula:

$$Al_2(OH)_{6-nx}A_x$$

wherein $x$ may vary from greater than 0 to less than 6, $6-nx$ is greater than or equal to 0, $n$ is the valence of A, and A is selected from the group consisting of halide, nitrate, sulfamate, sulfate and mixtures thereof;

b. a zirconium compound selected from trioxodizirconium salts and the group having the general empirical formula:

$$ZrO(OH)_{2-nz}B_z$$

wherein $z$ may vary from 0.9 to 2, $n$ is the valence of B, $2-nz$ is greater than or equal to 0, and B is selected from the group consisting of halide, nitrate, sulfamate, sulfate and mixtures thereof; and c. a salt of an alkaline earth metal, the cation of said salt being selected from the group consisting of magnesium, calcium and mixtures thereof, and the anion of said salt being such as to produce a highly ionized alkaline earth metal in an acidic solution, said compounds being present in such amounts as to yield an Al/Zr mole radio of about 10:1 to 1:10, and said alkaline earth metal salt being present in such amounts that the weight ratio of alkaline earth metal to aluminum plus zirconium is about 1:1000 to 1:30.

2. An antiperspirant composition wherein the complex of claim 1 is dissolved in an aqueous solution such that the total amount of aluminum plus zirconium in the solution, calculated as the oxides, is about 5 to 15 weight percent, and the pH of the solution is at least about 3.

3. An antiperspirant composition according to claim 2 wherein said alkaline earth metal is magnesium.

4. An antiperspirant composition according to claim 3 wherein the alkaline earth metal salt is selected from the group consisting of magnesium halide, magnesium nitrate, magnesium sulfamate, magnesium phenolsulfonate, magnesium carbonate, magnesium hydroxide, magnesium oxide and mixtures thereof.

5. An antiperspirant composition according to claim 2 wherein said alkaline earth metal is present in the solution in an amount of about 0.1 weight percent or less.

6. An astringent complex according to claim 1 wherein $x$ varies from about 1 to about 2.

7. an astringent complex according to claim 1 wherein A is chloride or bromide.

8. An astringent complex according to claim 1 wherein B is chloride and $z$ is about 1.

9. An astringent complex according to claim 1 wherein B is bromide and $z$ is about 1.

10. An astringent complex according to claim 1 wherein the Al/Zr mole ratio is about 4:1 to 1:1.

11. An astringent complex according to claim 1 wherein said complex also includes aluminum chloride.

12. An astringent complex according to claim 1 wherein said complex is in the form of a powder.

13. A powder-in-oil antiperspirant composition comprising an aerosol propellant, oil and the complex according to claim 12 wherein said complex is present in an amount of about 1–6 weight percent of the antiperspirant composition.

14. An antiperspirant composition according to claim 2, wherein said complex also includes a buffer compound in sufficient amount to maintain the pH of the complex in aqueous solution between about 3 and 5.

15. An antiperspirant composition comprising an aqueous solution containing about 10 percent by weight of a complex comprising 5/6 basic aluminum chloride, zirconyl chloride and a trace amount of magnesium carbonate, said solution having a pH of about 4 and assaying approximately 1.5 weight percent aluminum, 1.4 weight percent zirconium and 0.01 weight percent magnesium.

16. A method of inhibiting perspiration comprising applying the composition of claim 2 to the human axilla.

17. A method of inhibiting perspiration comprising applying the composition of claim 15 to the human axilla.

18. A method of inhibiting perspiration comprising suspending the dried complex of claim 1 in an aerosol propellant, said complex being persent in the aerosol propellant in an amount of about 1 to 6 weight percent of the propellant, and spraying the resulting suspension on the human axilla.

* * * * *